(12) United States Patent
Löffler et al.

(10) Patent No.: US 7,118,523 B2
(45) Date of Patent: Oct. 10, 2006

(54) DEVICE AND METHOD FOR LOADING HOLLOW IMPLANTATION NEEDLES WITH CHAINS OF RADIATION SOURCES FOR INTERSTITIAL BRACHYTHERAPY OF TISSUE

(75) Inventors: Edgar Löffler, Berlin (DE); Günther Mondry, Berlin (DE); Florian Bornschein, Berlin (DE); Andreas Müller, Berlin (DE)

(73) Assignee: Eckert & Ziegler Eurotope GmbH, Berlin (DE)

( * ) Notice: Subject to any disclaimer, the term of this patent is extended or adjusted under 35 U.S.C. 154(b) by 0 days.

(21) Appl. No.: 10/359,547

(22) Filed: Feb. 6, 2003

(65) Prior Publication Data

US 2004/0111004 A1     Jun. 10, 2004

(30) Foreign Application Priority Data

Feb. 6, 2002  (DE) ............................... 102 04 818

(51) Int. Cl.
 *A61N 5/00*   (2006.01)
(52) U.S. Cl. ............................................. 600/3; 600/8
(58) Field of Classification Search ................ 600/1–8, 600/439, 459, 585, 427, 407, 411; 250/370.11, 250/507.1; 601/2–4; 604/22, 57–61, 164.01; 376/158, 202; 424/1.29, 422; 534/697, 534/696.7 D; 251/124, 121; 976/DIG. 350; 536/696–700

See application file for complete search history.

(56) References Cited

U.S. PATENT DOCUMENTS 4,697,575 A * 10/1987 Horowitz ....................... 600/8

(Continued)

FOREIGN PATENT DOCUMENTS

DE          0 466 681        1/1992

(Continued)

OTHER PUBLICATIONS

Palos, Bernice B., et al. "A Method for Inserting I-125 Seeds Into Absorbable Sutures for Permanent Implantation in Tissue", Int. J. Radiation Oncology Bio. Phys., vol. 6 (1980) pp. 381-385.

(Continued)

*Primary Examiner*—Samuel G. Gilbert
(74) *Attorney, Agent, or Firm*—Norris McLaughlin & Marcus PA

(57) ABSTRACT

The invention relates to a device and a method for loading hollow implantation needles with radiation sources made of radiation source chains, and a radiation source chain for interstitial brachytherapy of tissue.

It is the object of the invention to develop a device and a method for packing and feeding of radiation sources made of radiation source chains as well as a radiation source chain for interstitial brachytherapy of tissue, whereby a precisely metered quantity of connected radiation sources (seeds) that has been predefined for implantation, and optionally of spacers, can be inserted without remnants into hollow needles located inside or all designed of tissue to be treated, by simple and reliable manipulation without manual intervention. The design safely guides the contiguous seeds through hollow needles with low-friction, reduces the risk of a malfunction and allows optimal cleaning and/or sterilization, while also reliably protecting the surroundings from radiation. The problem is solved, among others, by a device which has at least one supported, drivable cylindrical magazine (10) for winding the radiation source chain (1), at least one drive system for transporting the radiation source chain (1) from the magazine (10) into a guide system (12) and feeding the radiation source chain (1) into the tip of a hollow needle (19) coupled to the guide system (12). Also provided are a device (8) for separating/cutting the radiation source chain (1) at a defined location as well as a control device for preventing damage to the sheath of the radiation sources (seeds). All essential components of the device are surrounded by a radiation-absorbing housing.

29 Claims, 8 Drawing Sheets

U.S. PATENT DOCUMENTS

| | | | | |
|---|---|---|---|---|
| 4,784,116 | A | * 11/1988 | Russell et al. | 600/8 |
| 4,815,449 | A | * 3/1989 | Horowitz | 600/7 |
| 5,242,373 | A | 9/1993 | Scott et al. | |
| 5,322,499 | A | 6/1994 | Liprie | |
| 5,851,172 | A | 12/1998 | Bueche et al. | |
| 5,860,909 | A | 1/1999 | Mick et al. | |
| 5,928,130 | A | * 7/1999 | Schmidt | 600/7 |
| 6,010,446 | A | 1/2000 | Grimm | |
| 6,273,851 | B1 | 8/2001 | Slater et al. | |
| 6,371,903 | B1 | * 4/2002 | Blanc et al. | 600/2 |
| 6,458,068 | B1 | * 10/2002 | Ellard et al. | 600/1 |
| 6,497,645 | B1 | 12/2002 | Halpern | |
| 6,530,875 | B1 | * 3/2003 | Taylor et al. | 600/7 |
| 6,558,309 | B1 | * 5/2003 | Hogendijk et al. | 600/7 |
| 6,673,006 | B1 | * 1/2004 | Winkler | 600/1 |
| 6,709,381 | B1 | * 3/2004 | Munro, III | 600/3 |
| 6,761,680 | B1 | * 7/2004 | Terwilliger et al. | 600/8 |
| 2003/0097035 | A1 | * 5/2003 | Tucker et al. | 600/8 |
| 2003/0171637 | A1 | * 9/2003 | Terwilliger et al. | 600/1 |
| 2004/0015037 | A1 | * 1/2004 | Rapach et al. | 600/1 |
| 2004/0097780 | A1 | * 5/2004 | Otsuka | 600/7 |

FOREIGN PATENT DOCUMENTS

| | | |
|---|---|---|
| EP | 0 172 288 A1 | 2/1986 |
| EP | 0 292 630 A1 | 11/1988 |
| EP | 0 576 101 A1 | 12/1993 |
| EP | 0 668 088 A1 | 8/1995 |
| EP | 1 070 519 A1 | 1/2001 |
| FR | 0278 829 B1 | 3/1993 |
| WO | WO 97/22379 | 6/1997 |
| WO | WO 99/15235 | 4/1999 |
| WO | WO 00/64538 | 11/2000 |

OTHER PUBLICATIONS

Scott, W.P., "Surgical Radiation Therapy With Vicryl-$^{125}$I Absorbable Sutures", Surgery Gynecology & Obstetrics, vol. 142 No. 5 (May 1976) pp. 667-670.

* cited by examiner

DEVICE AND METHOD FOR LOADING HOLLOW IMPLANTATION NEEDLES WITH CHAINS OF RADIATION SOURCES FOR INTERSTITIAL BRACHYTHERAPY OF TISSUE

The invention relates to a device for packing radiation sources and feeding those radiation sources from radiation source chains as well as a radiation source chain according to the preamble of claims 1, 22 and 29.

The device is intended to make packing and feeding the radiation sources simpler and more reliable.

Various methods and devices for permanent interstitial brachytherapy of tissue using radiation sources are known.

U.S. Pat. No. 5,242,373 (Scott) discloses an instrument for implanting radioactive seeds in the body. The instrument includes several components: a thin stationery support rod or support piston and another thin rod (mandrin) spaced apart from and parallel to the support rod, and being held in this relationship by two clamping blocks. The mandrin has through bores allowing it to move in the clamping blocks in a longitudinal direction. One block operates as a stop block, the other as a movable guide rail for the mandrin. The instrument also includes an elongated magazine which also has a through channel with several spaced seeds. The seed spacing is provided by spacers made of a bio-resorbable material. The entire system is completed with hollow implantation needles which are pierced into the tissue to be treated.

The application takes place in several steps: after the hollow needle is pierced into the desired tissue region, the magazine filled with radioactive seeds is coupled to the hollow needle by way of an adapter so that both through channels are superpositioned in proper alignment. The tip of the mandrin is then inserted into the proximal end of the magazine and pushed by the movable guide block along the main rod until it contacts the stopper. The entire content of the magazine is thereby supplied to the tip of the hollow needle. Accordingly, the distance between the stopper and the movable guide blocks, i.e. the stroke, which must be adjusted each time before the magazine is fed, is a critical parameter for correctly feeding the seeds into the needle tip.

The empty magazine is subsequently slowly retracted along the mandrin up to the stopper. Since the magazine and the needle are coupled together, the hollow needle is also retracted from the body, leaving the seeds and the spacer in the patient's body.

This configuration was improved further in U.S. Pat. No. 5,860,909 which, unlike the system disclosed in U.S. Pat. No. 5,242,373, consists of an arrangement of elements that can move relative to one another along only one motion axis.

The applicator includes a hollow needle which is pierced into the prostate in a conventional manner. The needle is releasably coupled with a needle chuck, which is slidably mounted with respect to a base member. For the duration of the implantation, the base member remains stationary with respect to the orientation to the patient. A seed magazine which does not include spacers, but only radioactive radiation material, is inserted into the needle chuck with a predetermined orientation perpendicular to the motion axis. The seeds are held in the magazine by a spring clamp, which is configured to hold only a single seed in a through channel formed by two opposing bores. A seed is transported through the hollow space of the applicator to the tip of the snap-on needle by a mandrin which passes through the application channel formed after the connection has been established.

For moving the needle chuck relative to the base member, there are provided predetermined notched lines with different spacings which allow the needle to be retracted relative to the applicator body to a constant position of the mandrin for placing a seed into the interior of the prostate. The needle tip thereby has a previously defined spacing to the released seed. The desired number of radiation sources can be supplied to the needle tip by repeatedly retracting and advancing of the mandrin, whereby each time exactly one seed reaches the insertion channel, aided by the spring force in the magazine.

These systems are disadvantageously unreliable. For example, the radiation sources can jam in the magazine, or the mandrin can be bent, so that the procedure may have to be interrupted or terminated or a new magazine or applicator may have to be used. In addition, several seeds may be implanted at the same location.

As a further disadvantage, several magazines may have to be used since a single magazine can only hold a maximum of 15 seeds, whereas up to 100 seeds—depending on the size of the prostate—are required for a procedure.

WO 97/22379 describes monitoring seed ejection with fiber optics. The described implantation system consists of an integrated hollow needle with a through bore enabling feeding of seeds. A thin rod which is also integrated in system has a length suitable to implant the seeds residing in the system magazine from the system through the needle into the tissue. A combined optical module provides a visual support for the attending physician who can thereby control the surgical procedure and view the result of the seed ejection.

The system is operated manually with a pull lever which is attached to a handle and controls the seed implantation.

The radiation sources should not change their implant location after the surgery, although seed are known to shift in the body. Although the loss of individual seeds does not necessarily significantly degrade the quality of the applied therapeutic dose for the organ, such losses should be prevented since individual seeds can be discharged through the urethra.

In addition to using individual loose seeds, there exists another method wherein implants are inserted into the tissue in a firmly connected configuration by using a bio-resorbable material (e.g., suture), in which the sources are embedded. This configuration is intended to prevent the aforedescribed risk of seed shifts in the body.

This type of seed chains or threads can be formed, for example, of the radiation sources themselves, possibly with additional spacers as well as a resorbable material in which the implants are enclosed and held together.

An article by Palos et al. (Int. J. Rad. Oncol. Biol. Phys. 1980, Vol. 6, pp. 381–385) describes in detail the insertion of seeds in a resorbable suture material for permanent implantation into diseased tissue.

Another article by Scott (Surgery, Gynecology & Obstetrics, 1976, vol. 142, pp. 667–670) describes different implantation methods for applying iodine-125 seeds in resorbable Vicryl® suture, which disadvantageously require a relatively complex manual manipulation.

EP 0 292 630 (Horowitz) discloses various feed systems for radiation therapy in diverse applications, among others also for the interstitial brachytherapy of prostate carcinoma. In a preferred embodiment, the radioactive seeds are introduced into a bio-resorbable material of the aforedescribed type in a predetermined arrangement (for example axially). The base material should preferably retain its stability for one to fourteen days and should be absorbed in the tissue 70 to 120 days after implantation.

The sources can have the geometric shape of, for example, a needle and/or cylinder with a plane tapered tip and a length that is significantly greater than the diameter. Several mechanisms relating to the composition and to the packing methods are described. The regions between the seeds can be provided with corresponding recesses that function as "rated break points." In addition, segments can be formed from seeds surrounded by a carrier material wherein the desired form of the radiation sources is obtained by connecting recesses at a bottom portion with projections at a tip portion (having a slightly smaller diameter). In another embodiment, seeds and spacers made of bio-resorbable material are inserted in a hollow tube made of the aforedescribed carrier material, with the tip of the hollow tube again tapering to a point.

An important feature of the carrier material is the rigidity of the resulting radiation source, allowing it to be inserted into the tumor tissue in a controlled manner and with a straight motion. Any deformation of the base material could impede or complicate this process.

EP 0 668 088 (Langton) describes a device and a method for producing and/or handling a support arrangement for radioactive seeds. The seed support consists again of bio-resorbable material, for example braided Vicryl® made of several strands.

The device consists of a rod-shaped container with a continuous surface, characterized by recesses with a constant spacing—on one hand, for the seeds and, on the other hand, for the (intermediary) suture material—, so that the entire radiation source chain can be accommodated.

A protective sheath adapted to absorb the ionizing radiation emitted by the seeds can be placed over the arrangement.

This arrangement is intended to secure the prefabricated base material with the enclosed seeds in the aforedescribed recesses, so that the spacing between the seeds remains constant. The entire arrangement is subsequently subjected to a specific thermal process. As a result, the enclosed radiation source chain attains a particular rigidity which depends on the process parameters (temperature, pressure, time, etc.). The predetermined spacing of the seed recesses maintains the mutual spacing between the radiation sources during and after the thermal process. The attained rigidity improves handling of the seed chains, in particular during insertion into a hollow needle.

Increasingly, in clinical applications, this arrangement has shown a serious disadvantage: the seed chain can block the interior of the hollow implantation needle, in particular when liquids (e.g. blood) enter the interior of the needle and contact the strands. This makes it more difficult to exactly place the seeds in the prostate. Also, the procedure can be delayed and the costs for the surgery can increase due to the amount of strands rendered unusable.

Accordingly, there is a need for an optimized arrangement of connected radioactive seeds which can be easily guided through the hollow needles with low friction.

The embodiment described in EP 0 668 088 has a further disadvantage in that the radiation source chains are difficult to prepare and to handle after delivery to the user: the aforedescribed container contains a maximum of 10 seeds. To prepare for an implantation, the required number of seeds must be packaged according to the surgical and dosage planning. To accomplish this, the links between the seeds have to be manually cut—after the outer sheath of the container has been removed—, so as to separate and remove from the seed chain the desired number of seeds that correspond to the dosage plan. This exposes the personnel preparing the seeds for implantation to radiation.

Finally, the PCT application WO 00/64538 (Reed) discloses another radioactive radiation source for brachytherapy. The employed carrier material should be bio-resorbable, substantially rigid, and in the form of an elongated homogeneous strand. In addition, various methods for inserting and securing the seeds are described.

EP 1 070 519 (Kindlein) describes a modular device and a processor-controlled method for inserting individual seeds and spacers from separate circular magazines into hollow needles which are already placed at predetermined implantation locations in the tissue.

One embodiment of the device includes the following components:

an electronic control module which stores the feed requirements of the individual implantation components within the main device according to a patient-specific dosage plan and controls the mechanical operation, and a corresponding loading mechanism which initially fills an intermediate storage device provided with several channels so that an electronically controlled and driven feed module, for example a wire, can transport the implant components located in the magazines from the magazine positions into these channels.

The seeds and bio-resorbable spacers are packaged along the edge of circular holders which are rotatably supported in a housing. The packing is characterized in that a respective seed or spacer is moved on the circular arc defined by the rotation into a through channel formed in the housing by two opposing bores, so that the feed wire transports the seed or spacer from the magazine into the following channel which functions as an intermediate storage.

The seeds and/or spacer arrangements disposed in the intermediate storage channels are transported so that after the hollow needle is connected to the distal position of the channel, with the hollow needle being located in a coordinate system defined by the therapy plan, for example by a perforated grid, a feed wire pushes the implantation arrangement consisting of the seeds and the spacers into the tip of the hollow needle. The feed wire is moved by an electromechanical drive and controlled by a processor. A system-integrated device, which is coupled to the needle and retracts the needle after the seeds are inserted, ensures that the implantated arrangement of seeds and spacers remains in the tissue, while the feed wire retains its most forward position when the needle is retracted.

This system can disadvantageously spread contaminated body fluids, such as a blood, through the feed wire, which is guided so as to make contact with a relatively large interior surface area in this system, among others, the magazine with seeds and spacers.

The conventional automated systems have a relatively complex construction and increasingly use electronic components which have to satisfy demanding requirements in clinical applications. Moreover, these devices can malfunction, and cleaning and sterilization can be particularly challenging and may not always be feasible for all the sensitive parts.

In addition, not all systems are adapted for feeding seed chains, although such chains are used in Europe in approximately 50% of all cases for interstitial brachytherapy of the prostate.

It is therefore an object of the invention to provide a device and a method for packing and feeding radiation sources made of radiation source chains and a radiation source chain for interstitial brachytherapy of tissue, which obviate the disadvantages of conventional devices, methods and radiation source chains, and which are simpler and safer to handle when feeding a predetermined, precisely metered quantity of connected radiation sources (seeds) to hollow needles for implantation. The hollow needles can be placed inside or outside of tissue to be treated. The construction should allow a reliable guiding and a low-friction passage of the connected seeds through hollow needles, should minimize the risk of a malfunction and allow optimal cleaning and/or sterilization and should reliably protect against radiation.

The object is solved by the features of the device according to claim 1 and by the features of the method for packing and feeding radiation source chains according to claim 22 as well as by the features of the radiation source chain according to claim 29.

The device for loading of hollow implantation needles with radiation sources from radiation source chains for interstitial brachytherapy of tissue is characterized in that there is provided at least one supported, drivable cylindrical magazine for winding the radiation source chain and at least one drive system for transporting the radiation source chain from the magazine into a guide system. The radiation source chain is pushed sufficiently far into the guide system so that it comes to rest under the cutting device where a partial chain containing a defined number of seeds is cut. The device also includes the aforementioned device for severing the radiation source chain, as well as a control device for checking the correct positioning of the radiation source chain before cutting, so that the sheath of the radiation sources is not damaged during the cutting process. The cut partial chain is then pushed by the drive or by other drives to the tip of a connected hollow needle. All essential components of the device are enclosed in a radiation-absorbing housing.

The method for packing a partial radiation source chain and for introducing the partial chain into hollow needles and/or directly into a tissue is characterized in that a device for feeding and cutting the radiation source chain from a magazine is coupled to the hollow needle, wherein the radiation source chain, corresponding to the desired number of seeds, is withdrawn from the magazine and fed to the cutting device, where the radiation source chain is cut and introduced into the hollow needle and thereafter through the hollow needle into the patient.

The radiation source chain, consisting of alternating radiation sources and bio-resorbable spacers, held together by a likewise bio-resorbable sheath, is characterized in that the spacers have a particular shape and that the sheath of the chain is dyed or marked differently at the respective positions of radiation sources and spacers, so that the position of the spacers within the chain can be unambiguously identified by optical means.

The geometry of the spacers is essentially cylindrical, the diameter of the spacers must not exceed the diameter of the employed seeds and the length of the spacers has to be selected so that the distance between adjacent seeds in the chain corresponds to the therapeutic standard. In a particular embodiment, the employed spacers may have a reduced diameter (throat). Such radiation source chain is sufficiently long so as to contain the entire seed energy necessary for treating a patient. This radiation source chain is introduced into a magazine with radiation-shielding walls. This magazine serves as a storage container and can be coupled to the device. A drive mechanism moves the magazine and additional guide elements so that the chain is moved out of the magazine and introduced into the guide system of the device.

The radiation source chain is packaged, i.e., partial chains which each contain their therapeutically required quantity of seeds are cut off and introduced into the corresponding hollow implantation needle. The needle can already be inserted in the patient or can be filled in preparation for surgery.

The entire process can be handled with little manipulation by an operator, thereby providing an optimal protection against radiation. The device is designed so that it can be reliably cleaned and sterilized.

By using the device and the method according to the invention, a sufficient number of seeds for an implantation, for example in the prostate, is provided.

If a portion of the radiation source chain is left over at the end of the treatment, then this portion can be returned to the magazine and disposed of with the magazine.

In a preferred embodiment, the magazine consists of a cylindrical storage roll or spool, about which the radiation source chain is wound for support. The entire feed system and the magazine are surrounded by a housing which offers sufficient protection from the ionizing radiation emitted by the radiation source chain.

Preferably, the spool has a groove with a depth that is optimized for the outer diameter of the radiation source chain, with the radiation source chain being inserted into the groove. The groove forms a spiral on the spool, so that the radius of curvature of the chain remains constant during winding and unwinding.

The spool body is also part of a drive, which transports the radiation source chain or parts thereof from the storage position (wound on the spool) via a guide system to the tip of a hollow needle coupled to the device. For this purpose, at least one additional drive is provided which moves the radiation source chain inside the guide.

A further component of the device is a unit for controllably cutting the radiation source chain, with the cut being made solely at a predefined location, while at the same time preventing damage to the seed sheath. In this way, the number of connected seeds and spacers required for filling the hollow needle is provided in the form of a partial chain.

In another embodiment, the cutting device consists, for example, of a moving metal disk, which cuts the bio-resorbable spacer in the center with an (eccentric) circular motion. The disk is sufficiently sharp along the edge and the force applied to the object to be cut is sufficiently large to cut the spacer material, but not sufficient to damage the metal sheath of the seeds.

In another embodiment, the disk is replaced by a knife-like object performing a vertical cutting motion.

In yet another embodiment, a thermal cutting device is employed, wherein for example the chain is cut in a vertical motion with a heated wire at the position of a spacer. This advantageously prevents damage to the seed sheath.

Different methods can be used for controlling a defined cutting location:

One method includes mechanically controlling the drive for the radiation source chain, so that the radiation source chain advances sequentially in discrete steps. By selecting a suitable number of steps—the length of the steps is already defined by the total length of a seed and a spacer—and a spatial configuration of the cutting system, only the spacers of the radiation source chain come to a halt inside the cutting region, so that the radiation source chain is always cut at a predefined location. This method has the advantage that the cutting system does not require complex electronic controls, and can advantageously be used when an optical differentiation between the seeds and the spacers is difficult.

If the positions of seeds and spacers in the chain can be optically distinguished from the outside, for example by the aforedescribed different coloring or markings of the sheath, then the correct position of the radiation source chain can be easily checked visually or by using opto-electronic sensors.

In addition, radiation detectors or other sensors capable of measuring the location of the seeds can be used with such a control device.

These embodiments controlled by a sensor and/or detector can in addition be provided with a mechanism which allows the cutting operation to take place only when the chain is correctly positioned.

With such sensor and/or detector system, it is also possible to count the number of the chain elements of the partial chain to be cut off, thereby enabling control over the length of the respective partial chain, i.e., the number of the seeds contained therein, independent of the drive.

The guide or transport channels form additional integrated components of the supply system and guarantee reliable and stable guiding during the motion of the radiation source chain or packaged sections. The side of the guide facing the hollow needle is closed off by an adapter which is designed to reliably couple a hollow implantation needle and to provide an unobstructed transition from the guide piece into the lumen of the hollow needle.

The outlet of the coupling location (and hence of the entire device) is secured so that the interior of the guide passageways is opened and the packaged implant components can be transferred to the needle channel only when a hollow needle is connected. Such safety locks can be implemented, for example, with at least two mutually displaceable apertures or with spring-operated spherical closures.

Another component of the feed and packing system is an additional drive for a feed wire which pushes the packaged radiation source chain further into the needle tip—after the chain has been transported by the drive system of the radiation source chain into any intermediate region, where the feed wire remains, with the packaged partial chain remaining in the tissue when the needle is retracted. This separate additional drive element, for example a guide wire, is inserted into the guide system through a distinct separate access, thereby spatially separating the unpackaged radiation source chain from the guide wire, which reduces the risk of spreading of contaminants originating from body fluids, e.g., blood.

A control mechanism ensures that the wire enters the needle only behind a radiation source chain segment and cannot enter the connecting piece if the connecting piece is blocked by the radiation source chain. The wire should also not obstruct the advance of the radiation source chain, thereby eliminating the risk of damage to the radiation source sheath or its components.

In another embodiment—which relates in particular to the aforedescribed method for filling hollow needles before these are inserted in the tissue—the feed wire is omitted.

Moreover, the feed system enables the user to preselect the number of seeds to be packaged in the partial chain and subsequently loaded into the attached hollow implantation needle. The number of seeds is selected by controlling the radiation source chain drive and the cutting system.

In another embodiment, the preselected number of radiation seeds is provided through a specified rotation of all the drive wheels when the radiation source chain magazine is unwound to the cutting system. The preselected seed quantity corresponds to a discrete number of integer multiples of a revolution that depends on the mechanical design. After cutting, the feed length of the feed wire is matched to the obtained length of the cut-off partial section of the radiation source chain in such a way that when the radiation source chain partial section is at its end position, the geometric end point of the wire tip on the side facing away from the hollow needle is located inside the hollow needle. Accordingly, a relation exists between the number of seeds selected by the user and the travel path which represents information processed by the device.

The novel feed and packing system is constructed in a modular fashion in such a way that components which are particularly at risk from the aforedescribed bio-contamination, contamination, can be easily removed or cleaned and sterilized.

The entire device is also configured with an enclosure that provides radiation protection from the ionizing radiation produced by the radioactive seeds. In particular, the magazine in which the radiation source chain is stored is protected so that the quantity of seed material specified for an entire surgical procedure can be inserted and replaced with significantly less radiation exposure for the user than with conventional interstitial brachytherapy.

Additional advantageous embodiments of the invention are recited in the dependent claims.

An embodiment of the invention relating to the treatment of prostate carcinoma will be described hereinafter in greater detail. In the accompanying drawing is shown in.

Prostate tumors have emerged as the most frequent type of cancer in the male population and also the second most frequent cause of deaths on a percentage basis due to cancer.

In addition to applying heat and cold and hormone treatment, in particular radiation therapy—either alone or in combination with other methods—has become more prominent. Ionizing radiation damages the genetic material of cells. Cancer cells have a repair system that work less well than that of normal cells; accordingly, the inflicted damage cannot be as well repaired, so that the cancerous cells die.

In the temporary brachytherapy using the so-called afterloading technique, radiation sources are—depending on the dose to be provided—inserted into the tumor tissue only for a specified time. This is done with suitably placed seed passageways, for example catheters; the sources can be moved manually or automatically.

In this procedure, small encapsulated radiation sources which contain radio isotopes with a relatively short half-life and low-energy radiation characteristics (e.g., iodine-125 or Pd-103) are implanted close to or directly into the diseased tissue, where they remain permanently, conferring a therapeutic radiation dose to their surroundings, thereby destroying the cancer cells. The applied dose energy is hence significantly lower than in temporary therapy.

Permanent implants have a significant advantage over a limited form of therapy with the temporary implants in that invasive procedure on the patient only has to be performed once. In addition, the effective radius of permanent implants is limited due to the particular energetic properties of the isotopes, so that healthy tissue is not affected. The intent is to apply a homogeneous dose distribution to the diseased tissue while protecting from excess radiation difficult areas, such as the urethra, the seminal vesicles or the rectum.

This necessitates an exact placement of the seeds in the prostate.

Individual tomographic images of the organ and markings of the target area by the physician make it possible to use special software to develop a plan for positioning the radiation sources depending on the employed isotope and its activity.

A coordinate grid which is a reference for all ultrasound images of the prostate is oriented based on the acquired image. This virtual grid is implemented by a perforated grid plate which is aligned with reference to the longitudinal ultrasound axis and the motion direction of this axis. The perforated grid plate aids during surgery with the orientation for piercing the hollow needles.

The brachytherapy of prostate is performed in different ways which are distinguished essentially by the time the dose is planned and the implantation needles are filled.

In the dose is planned prior to surgery, the needles are loaded in preparation of the surgery according to the quantities determined in the dose plan. The needles are coupled to the device, the radiation source chain is transported out of the magazine according to the required number of seeds for the respective needle, the partial chain is cut off and then pushed forward to the tip of the hollow needle.

The needles are then pierced manually into the patient by the physician in the operating room, and the partial seed chains contained therein are placed in the prostate with the help of a mandrin.

When the dose is planned intra-operatively, the needles are initially pierced into the prostate under transrectal ultrasound image control, whereafter the dose is planned. In this case, partial chains with the therapeutically required number of seeds are not only packaged and inserted in needles, but the partial chains are placed directly using the device. Accordingly, the design of the device needs to be modified.

The process flow is a initially identical to the process flow with pre-operative planning; however, with the exception that the entire procedure is performed in the operating room and the needles that are to be attached are already placed in the patient. The device is herein connected with the target system base via a suitable support, thus preventing the transfer of detrimental forces to the needle and injury to the patient. After the packaged partial chain in this embodiment is pushed to the tip and then fixed by the mandrin-type advance system, the physician adjusts the distal placement position of the partial chain by adjusting the insertion depth of the needle according to plan. The seeds are placed by having a mechanism of the device retract the needle, while the partial chain is held in position by the aforedescribed advance mechanism, so that the partial chain cannot retract with the needle and remains in the prostate.

Figure 1:
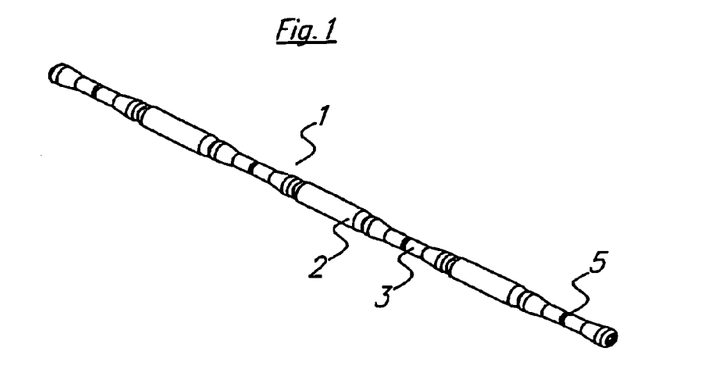
FIG. 1 a schematic perspective diagram of an employed radiation source chain.

FIG. 1 shows a perspective view of an embodiment of an employed radiation source chain 1. Clearly visible are the alternatingly arranged seeds 2 and spacers 3.

Figure 2A:
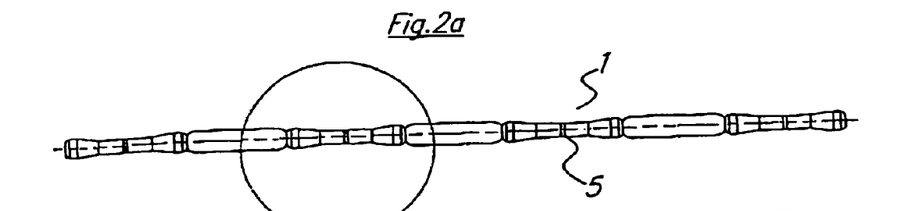
FIG. 2a a side view of the radiation source chain of FIG. 1.
Figure 2B:
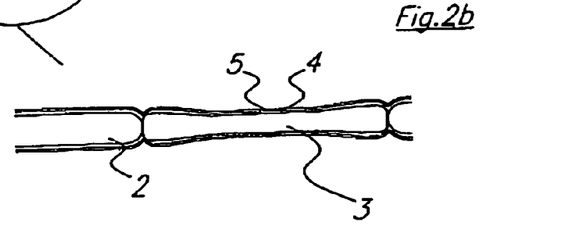
FIG. 2b an enlarged detail of the chain of FIG. 2a, with a spacer.

FIG. 2a shows the radiation source chain 1 according to FIG. 1 in a side view, and FIG. 2b shows a cross-sectional view of the detail outlined in FIG. 2a.

In this configuration of the radiation source chain 1 bio-resorbable spacers 3 are disposed between two seeds 2, which are surrounded by a sheath 4 which is also bio-resorbable. The spacers 3 have a throat to facilitate recognition by sensors and promote breakdown in the body of the patient after implantation. In a panicular embodiment, as shown in FIG. 2, the spacer may have a conical shape from either of its ends towards is center.

Markings 5 are placed on the sheath of the radiation source chain 5 for reliably identifying the position of the spacers 3 within the chain 1.

Figure 3:
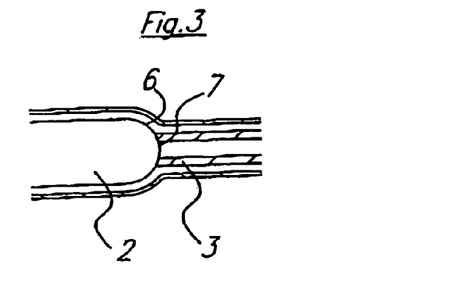
FIG. 3 an embodiment of the ends of the seed and spacer holder.

In an exemplary embodiment of the invention, "IsoSeed™" produced and distributed by the company Bebig Isotopen-und Medizintechnik GmbH is employed, and hollow spacers 3 are used, as shown also in FIG. 3. The spacers 3 are hollow to enhance their visibility in ultrasound images.

In general, the outside diameter of the spacers 3 is smaller than or identical to the outside diameter of the seeds 2.

FIG. 3 illustrates an embodiment of the end faces 7 of the spacers 3, shown here with the cavity, which directly contact the end faces of the seeds 6 and stabilize the elements of the radiation source chain 1. Taking into account the bending, compression and tensional forces acting onto the spools 10 during storage and during the motion in the guide system (FIG. 4) and the fact that in spite of these forces a constancy of the entire radiation source chain length is an important prerequisite for a reliable operation of the device and the implantation procedure, a convex form of the end faces 7 of the spacers that complements a concave form of the seed ends 6 represents an optimized configuration which enables rotation—similar to a ball joint—while at the same time providing a sufficiently large contact surface for transmitting pressure forces.

Figure 4:
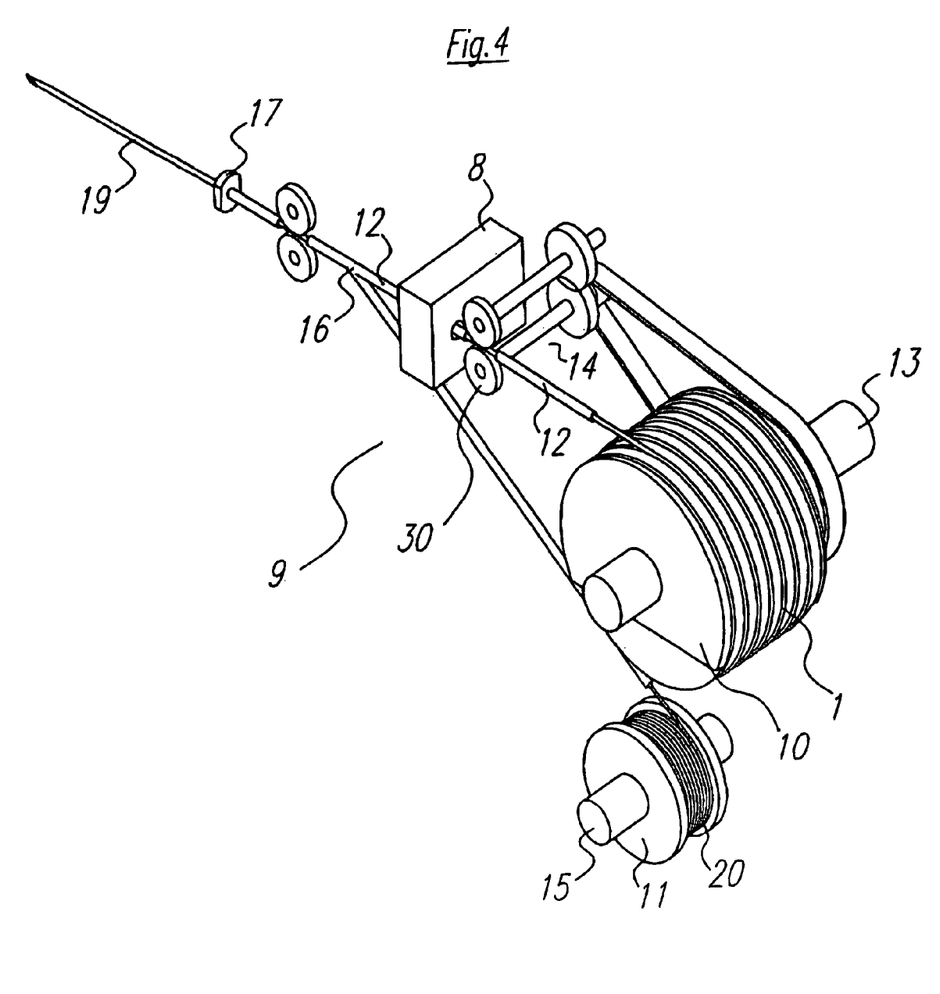
FIG. 4 a simplified schematic diagram of a feed system.

A schematic diagram of a possible embodiment of the feed and packing system 9 for the radiation source chain 1 is illustrated in FIG. 4.

Not shown is a housing that encloses the device and prevents emission of radiation to the surroundings.

A spool 10 with a drive axis 13, on which the wound-up radiation source chain 1 is placed, functions as a magazine for the radiation source chain 1. Positioned directly thereafter is the start of the guide system into which the radiation source chain 1 is inserted immediately after exiting the spool body 10. The guide system consists of a tube 12 with a suitable diameter. The motion of the radiation source chain 1 in the guide system can be stabilized by a suitably spaced second drive 14, which has two meshing wheels 30 which receive the portion of the radiation source chain 1 unwound from the spool 10 and transport that portion towards a cutting system 8.

The control and/or coupling of all drives 13, 14 that move a contiguous radiation source chain 1 is implemented so as to ensure a synchronous transport which prevents tension or compression in the radiation source chain 1 and damage to the chain 1.

The radiation source chain 1 is fed through an additional guide tube 12 to the cutting system 8 where the number of seeds 2 and spacers 3 specified by the user are packaged. An additional guide tube 12 follows which guides the radiation source chain 1 to a connecting piece 16 formed as a Y-tube.

This connecting piece 16 operates as a feed unit which preferably is also a tubular section made of metal; it serves exclusively as a passageway for a guide and/or feed wire 20 that is unwound from a spool-like magazine 11. The wire 20 enters the main feed tube 12 and advances the packaged implant components towards the hollow implantation needle 19. For this purpose, the spool 11 of the guide wire 20 has its own drive 15.

The end section of the guide tube 12 is terminated by a coupling mechanism in the form of an adapter 17, to which suitable hollow implantation needles 19 are connected such that the radiation source chain 1 can be inserted into the needle lumen without obstruction.

Figure 5A:
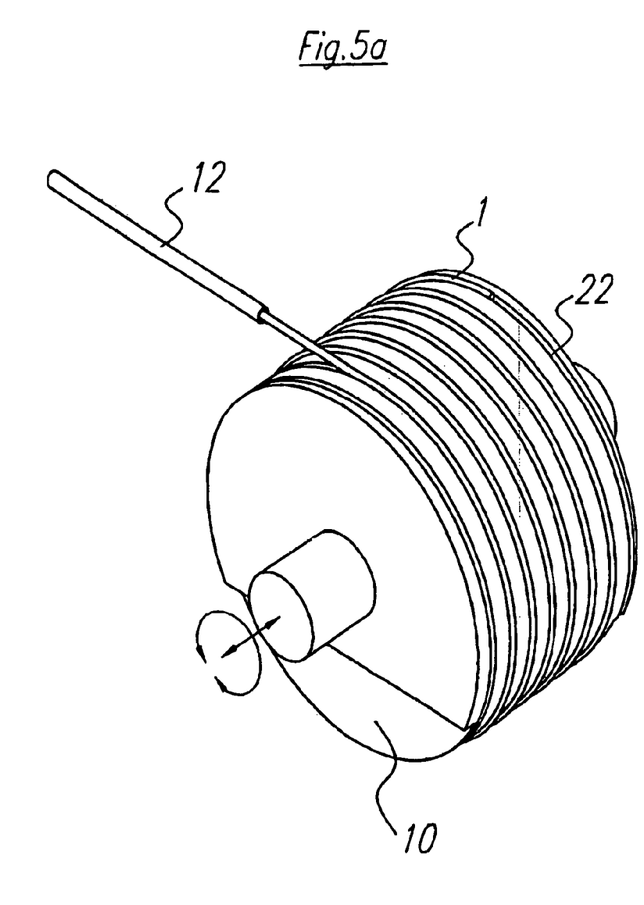
FIG. 5a a schematic perspective diagram of a spool with a wound radiation source chain, FIG. 5b a side view of the spool of FIG. 5a with the wound radiation source chain, FIG. 6 a schematic diagram of the drive system for feeding the radiation source chain to the cutting system, FIG. 7 a schematic diagram of the cutting system, FIG. 8 a schematic diagram of the magazine of the wire guide, FIG. 9 a schematic diagram of the connection location, where the guide wire enters the channel of the radiation source chain, and FIG. 10 a schematic diagram of the end piece of the guide system with a coupling location for the hollow implantation needle.

FIG. 5a shows the spool 10 of the radiation source chain 1 in a perspective view. In this embodiment, the radiation source chain 1 is almost completely wound onto the spool body 10. The radiation source chain 1 is located into a groove 22 disposed in the surface of the spool body, with the groove 22 being optimally matched to the diameter of the radiation source chain 1 and providing stability against the forces acting perpendicular to the direction of the radiation source chain 1. The radiation source chain 1 is also wound with a constant bending radius such that the individual windings extend around the spool body 10 in a spiral and have a defined mutual spacing.

Figure 5B:
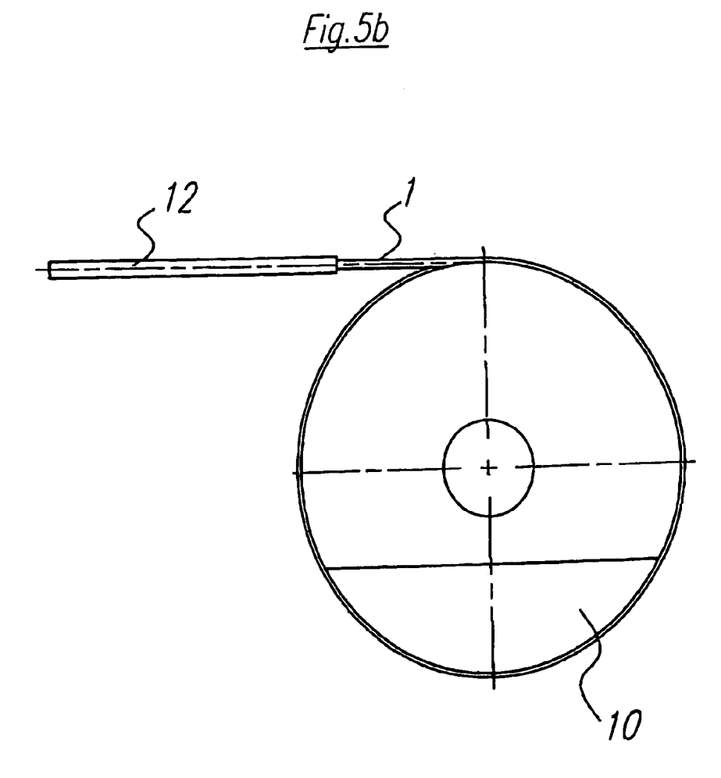

FIG. 5b shows in a side view the transition of the radiation source chain 1 into the guide tube system 12. With the tube opening at a defined stationery position, the spool 10 is supported such that the spool body 10 performs a translation in the direction of its rotation axis during rotation, so that the unwound radiation source chain 1 is always inserted into the tube entrance perpendicular to the spool axis.

Figure 6:
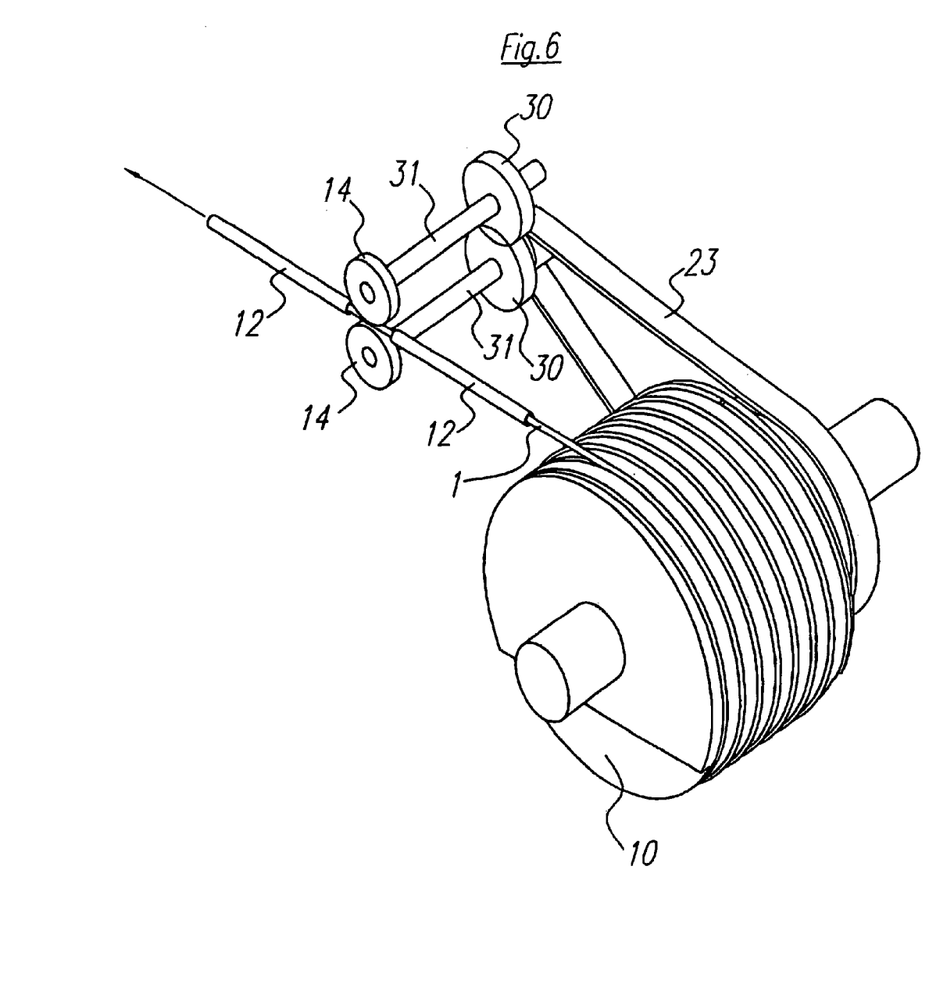

FIG. 6 shows an embodiment of the drive system assembly of the spool 10 and the secondary drives which feed the radiation source chain 1 to the cutting system 8. The spool 10 is provided with a drive wheel that is connected with the secondary drive 14 via a belt transmission 23. The secondary drive 14 consists of meshing gear wheels 30 which are each connected via a shaft 31 with the actual drive wheels 14 which transform the rotation into a translation of the radiation source chain 1. The guide tube 12 is discontinuous and thus provides direct contact with the radiation source chain 1. The pressing force on the radiation source chain 1 is adjusted according to a suitable profile so as to prevent slippage and damage to the components of the radiation source. The radiation source chain 1 can move both towards the cutting system 8 and, in the opposite direction, towards the spool 10.

Figure 7:
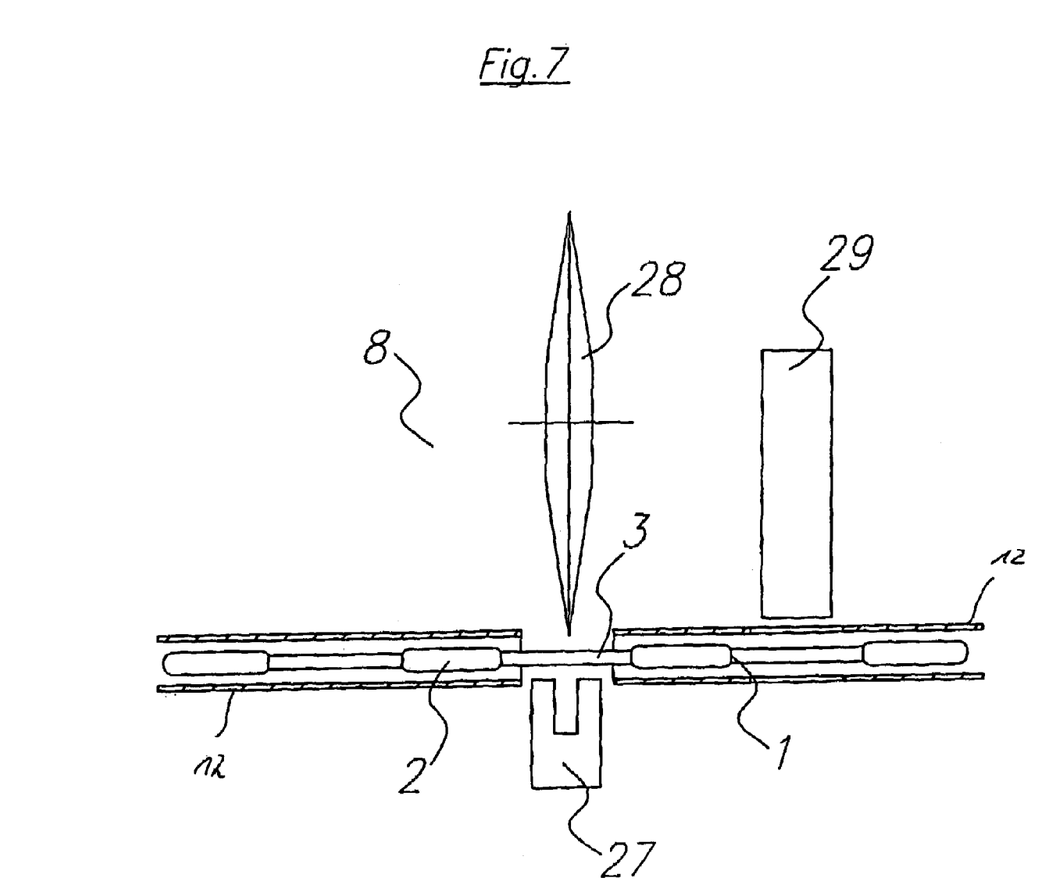

FIG. 7 shows a cross-section of the separation and/or cutting system 8 with the guide tube 12 that leads to the spool 10 and the hollow needle 19, and contains the radiation source chain 1. A number of seeds 2, as defined by the application, with interposed spacers 3 is located on the side of the apparatus leading to the hollow needle 19. The radiation source chain 1 is positioned to be cut under a cutting wheel 28, making sure that the spacer 3 is cut in the center. The cutting wheel 28 cuts in an (optionally eccentric) circular motion, whereby the drive is powerful enough to cut the material of the spacer 3 in a single motion. A support element 27 located below the spacer 3 prevents the radiation source chain 1 from being pushed out of the guide tube 12 by the force acting perpendicular on the guide tube 12. Before the spacer 3 is cut, the correct position of the radiation source chain 1 and/or of the spacer 3 to be cut are controlled by a sensor 29. At the end of the cutting operation, the cutting wheel 28 again assumes its initial position, thereby enabling the separated portion of the radiation source chain 1 (partial chain) to advance.

Figure 8:
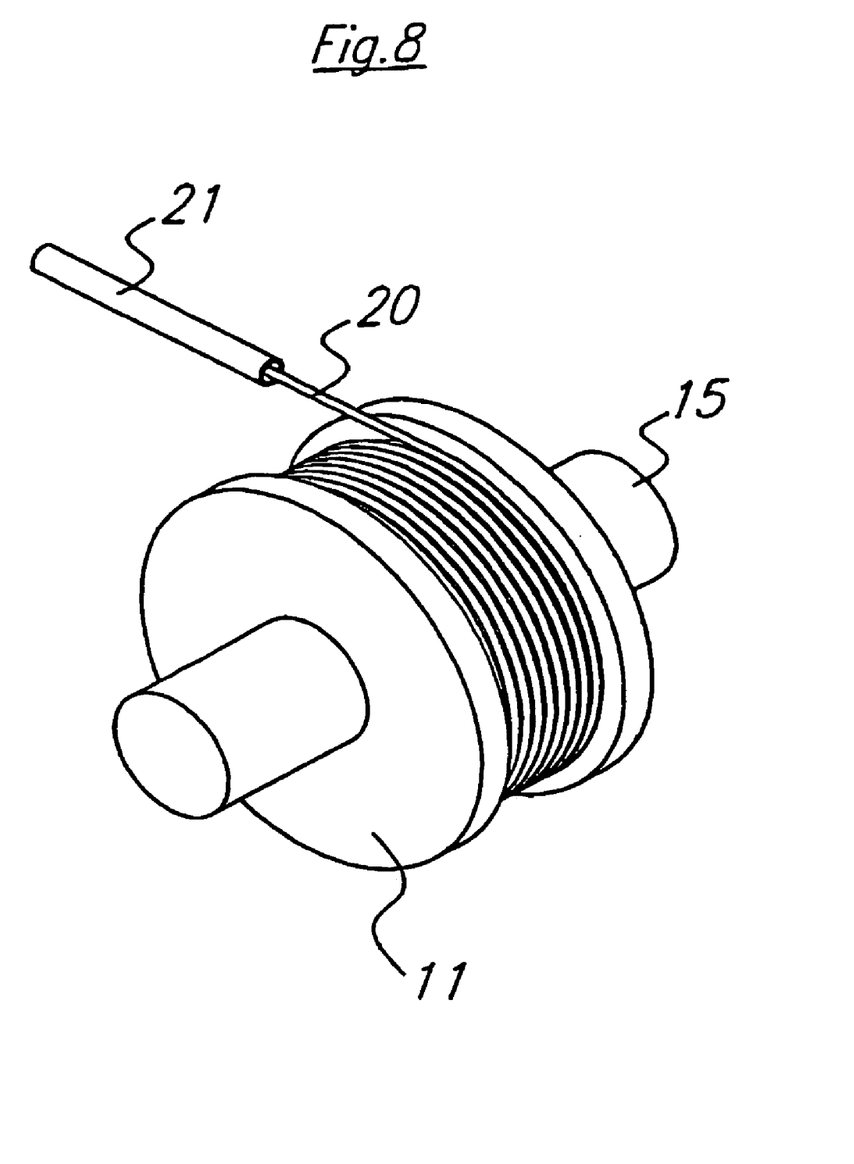

FIG. 8 shows the wire guide magazine 11 which is implemented as a spool. The wire 20 is made of a nickel-titanium alloy and is wound, like the radiation source chain 1, onto the spool 11 with a constant radius. The associated drive control allows the wire 20 to advance into the main channel 12 with the radiation source chain 1 only if the entrance location is not obstructed.

Figure 9:
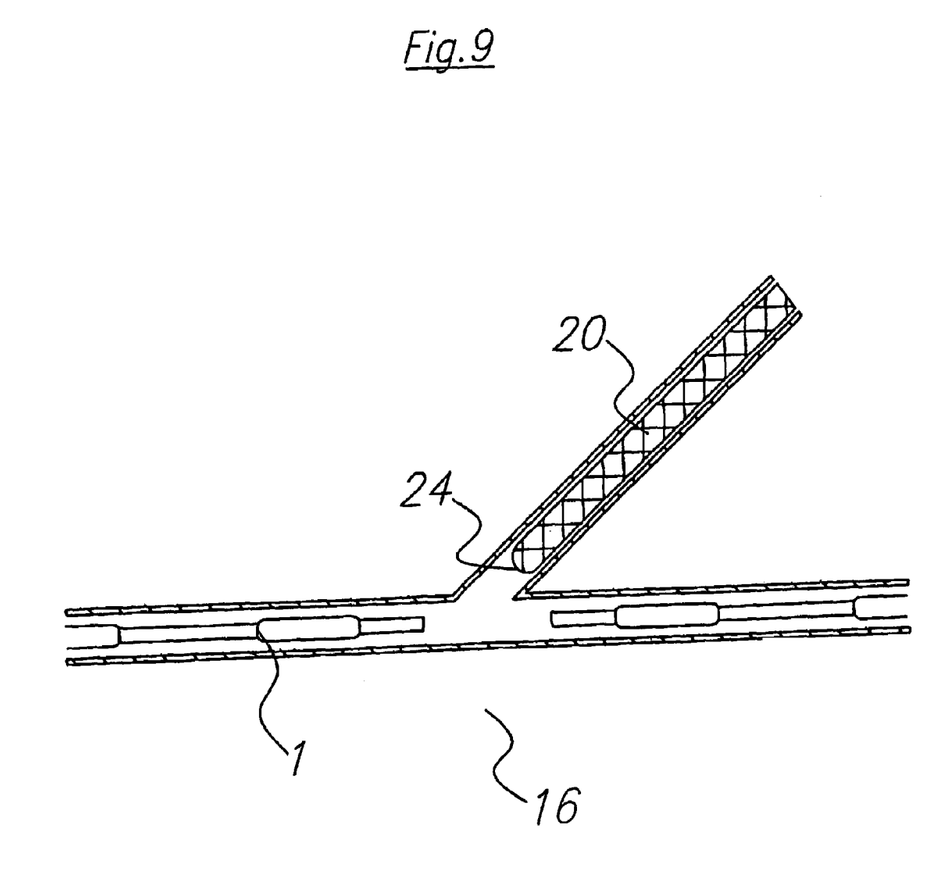

FIG. 9 shows the connecting piece 16, here implemented as a Y-tube, wherein the packaged portion of the radiation source chain (partial chain) has already been transported in the direction of the hollow needle 19 behind the entrance opening. The guide wire 20 driven out of the exit opening can be guided behind the separated section of the radiation source chain 1 (partial chain) to promote its further advance. In an exemplary embodiment, the wire tip 24 of the guide wire 20 is implemented as a hemisphere with a cross-section that matches the guide tube lumen and the diameter of the radiation source chain. This provides an optimal surface for the thrust transmitted to the radiation source chain 1, while simultaneously eliminating the risk of damage to the radiation source chain 1, for example by sharp corners.

In another embodiment (not shown), the wire tip 24 has a flat circular termination with rounded edges.

The feed length of the guide wire 20 matches the length of the packaged radiation source chain 1 (partial chain) according to the preselected number of seeds, so that each packaged radiation source chain 1 is reliably moved to the tip of the hollow needle 19. The portion of the radiation source chain 1 connected with the spool 10 is retracted towards the spool 10 behind the cutting system 8 to subsequently repeat the cutting process.

Figure 10:
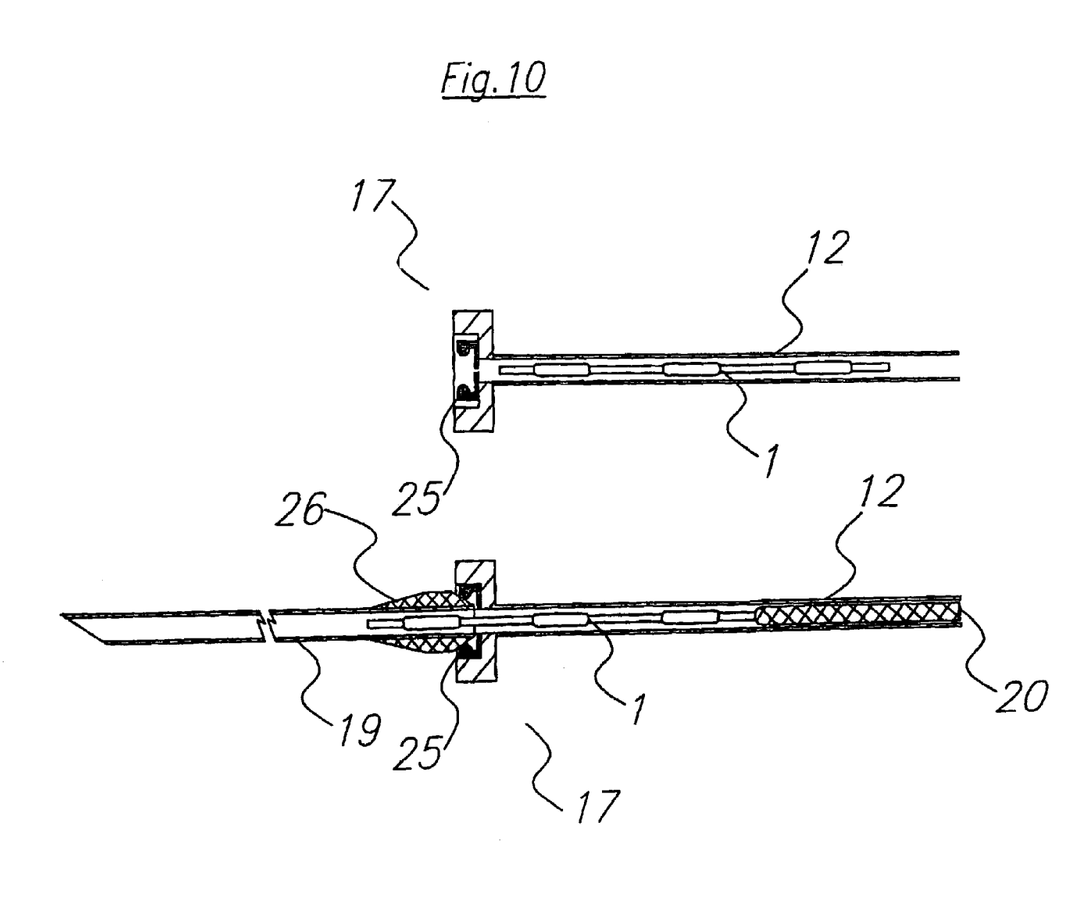

FIG. 10 shows the coupling location between the device and the hollow needle 19 for packing and feeding, with the closure system in an unopened (uncoupled) as well as in an open (coupled) state.

The adapter 17 closes the guide tube 12 and is large enough to receive the connecting end of the hollow needle 19. A two-piece aperture 25 provided with a spring mechanism closes the through channel by displacing the eccentric circular bore of the outer aperture 25 relative to the bore of the inner aperture 25. This prevents implant components from inadvertently exiting the device. To open the closure (adapter) 17, a hollow needle 19 with a matching piece 26, for example a female Luer-Lock adapter must be connected by a rotary motion in the outer opening of the guide tube 12, such that the bore of the outer aperture 25 is moved precisely over the bore of the inner aperture 25, thereby unblocking a through channel for the radiation source chain 1.

In another embodiment (not shown), the safety closure of the adapter 17 can also be implemented using two spheres which are urged against each other by a spring force. When the end piece of a needle having a termination ring that is larger than the outside diameter of the needle passes through, the two spheres are pressed over the ring perpendicular to the motion direction of the needle, so that they rest in their final position in a recess located on the side behind the termination ring, thereby fixing the entire needle.

It should be pointed out that the description of the invention is primarily directed to treatment of prostate carcinoma. However, this is not intended as a limitation of the disclosed invention, which can also have other medical applications. A large number of brachytherapy procedures are feasible wherein radioactive radiation source chains are implanted into tissue in vivo for providing an energy dose.

LIST OF REFERENCE NUMERALS 1 radiation source chain
2 radiation source (seed)
3 spacer
4 sheath
5 marking of the spacer position
6 seed end
7 spacer end
8 separating/cutting device
9 device for packing and feeding
10 spool body (magazine)
11 wire magazine
12 guide tube
13 drive axis
14 drive for radiation source chain
15 drive for wire magazine
16 connecting piece (Y-tube)
17 adapter
18 additional drive for 1
19 hollow implantation needle
20 guide wire
21 wire guide tube
22 groove
23 drive belt
24 wire tip
25 aperture
26 counterpart
27 support piece
28 cutting wheel
29 sensor
30 wheel
31 shaft

The invention claimed is:

1. Radiation source chain for injection into a hollow needle, comprising at least one modular radiation source and at least one modular bio-resorbable spacer, held together by a continuous bio-resorbable sheath surrounding said radiation source and said spacer, wherein the radiation source chain is flexible, an end face of the spacer and an end face of the radiation source directly contacting each other in at least one location on the source chain, such that the radiation source and the spacer are capable of bending with respect to each other at said location.

2. The radiation source chain according to claim 1, wherein
the spacer is elongated and has a diameter which is equal to at most the diameter of the radiation sources.

3. The radiation source chain according to claim 1, wherein the diameter of the spacer at its center is smaller than the diameter at its ends, to thereby form a throat.

4. The radiation source chain according to claim 3, wherein
the spacer has a conical shape from either of its ends towards its center when in both a deployed and non-deployed state.

5. The radiation source chain according to claim 1, wherein
the spacer has a tubular shape.

6. The radiation source chain according to claim 1, wherein the spacer is hollow.

7. The radiation source chain according to claim 1, comprising at least two radiation sources, wherein the length of the spacer is sufficient to guarantee that the distance between successive radiation sources corresponds to a selected standard.

8. The radiation source chain according to claim 1, wherein end faces of the spacer have a concave shape, and end faces of the radiation source have a convex shape, the end faces of the spacer and the end faces of the radiation source directly contacting each other in at least one location on the source chain, such that the radiation source and the spacer are capable of bending with respect to each other at said location.

9. The radiation source chain according to claim 1, wherein end faces of the spacer have a convex shape, and end faces of the radiation source have a concave shape, the end faces of the spacer and the end faces of the radiation source directly contacting each other in at least one location on the source chain, such that the radiation source and the spacer are capable of bending with respect to each other at said location.

10. The radiation source chain according to claim 1, further comprising a means for allowing a position of the spacer or the radiation source within the chain to be unambiguously identified via visible markers on an outside surface of the sheath.

11. The radiation source chain according to claim 10, wherein the differentiating means comprises a marking or color on the sheath associated with one of the radiation source and spacer.

12. The radiation source chain according to claim 1, further comprising a means for allowing a position of the spacer or the radiation source within the chain to be unambiguously identified, wherein the means for allowing a position of the spacer or the radiation source within the chain to be unambiguously identified comprises a shape of the spacer contrasting to a shape of the radiation source.

13. The radiation source chain according to claim 1, wherein tha spacer comprises a region which is cuttable by a means for cutting, wherein said region is hollow and empty.

14. The radiation source chain according to claim 13, further comprising a means for allowing the region which is cuttable to be unambiguously identified via means for visibly identifying said region which is cuttable by way of visible information on an outside surface of the sheath.

15. The radiation source chain according to claim 13, wherein the region which is cuttable is formed so as to be cuttable by a force sufficient to cut through the spacer, but which force is not sufficient to damage the radiation source.

16. A spacer for use with radiation sources to form a radiation source chain, comprising
a discrete bio-resorbable spacer, wherein the spacer is elongated and has a throat when in both a deployed and non-deployed state with respect to a radiation source chain, the diameter of said throat being smaller than the diameter of said spacer at its ends around the whole circumference of the spacer, end faces of the spacer being structured to allow direct contact with respective end faces of a radiation source to thereby provide a direct contact location, and wherein the spacer has a conical shave from its ends towards its center when in both a deployed and non-deployed state.

17. The spacer of claim 16, wherein the diameter of said spacer is equal to at most the diameter of the radiation source.

18. The spacer of claim 16, wherein the spacer is solid.

19. The spacer of claim 16, wherein the spacer is hollow and inflexible.

20. The spacer of claim 16, for use with radiation sources having convex or concave end faces, wherein the spacer is provided with a corresponding concave or convex form on its end faces, such that the radiation source and the spacer are capable of bending with respect to each other at said direct contact location.

21. The spacer of claim 16, wherein the spacer is provided with a concave form on its end faces, such that the radiation source and the spacer are capable of bending with respect to each other at said direct contact location.

22. A spacer for use with radiation sources to form a radiation source chain, comprising a discrete bio-resorbable spacer, wherein the spacer is elongated and has a throat when in both a deployed and non-deployed state with respect to a radiation source chain, the diameter of said throat being smaller than the diameter of said spacer at its ends around the whole circumference of the spacer, end faces of the spacer being structured to allow direct contact with respective end faces of a radiation source to thereby provide a direct contact location, and wherein the spacer is used with radiation sources having convex or concave end faces, the spacer being provided with a corresponding concave or convex form on its end faces, such that the radiation source and the spacer are capable of bending with respect to each other at said direct contact location.

23. The spacer of claim 22, wherein the diameter of said spacer is equal to at most the diameter of the radiation source.

24. The spacer of claim 22, wherein the spacer is solid.

25. The spacer of claim 22, wherein the spacer is hollow and inflexible.

26. A spacer for use with radiation sources to form a radiation source chain, comprising a discrete bio-resorbable spacer, wherein the spacer is elongated and has a throat when in both a deployed and non-deployed state with respect to a radiation source chain, the diameter of said throat being smaller than the diameter of said spacer at its ends round the whole circumference of the spacer, end faces of the spacer being structured to allow direct contact with respective end faces of a radiation source to thereby provide a direct contact location, and wherein the spacer is provided with a concave form on its end faces, such that the radiation source and the spacer are capable of bending with respect to each other at said direct contact location.

27. The spacer of claim 26, wherein the diameter of said spacer is equal to at most the diameter of the radiation source.

28. The spacer of claim 26, wherein the spacer is solid.

29. The spacer of claim 26, wherein the spacer is hollow and inflexible.

* * * * *